United States Patent [19]

Ostrowski

[11] 4,304,952
[45] Dec. 8, 1981

[54] USE OF TRIPHENYLBORON AS ALKYLATION INHIBITOR IN A LIGAND-COMPLEXING PROCESS

[75] Inventor: Paul C. Ostrowski, Webster, Tex.

[73] Assignee: Tenneco Chemicals, Inc., Saddle Brook, N.J.

[21] Appl. No.: 171,631

[22] Filed: Jul. 23, 1980

[51] Int. Cl.³ .................. C07C 7/10; C07C 7/148; C07C 7/156

[52] U.S. Cl. .................................... 585/848; 585/833

[58] Field of Search .......................... 585/348, 833

[56] References Cited

U.S. PATENT DOCUMENTS

| | | | |
|---|---|---|---|
| 3,592,865 | 7/1971 | Long et al. | 585/848 X |
| 3,651,159 | 3/1972 | Long et al. | 585/848 |
| 3,923,958 | 12/1975 | Turnbo et al. | 585/848 X |
| 3,927,176 | 12/1975 | Turnbo et al. | 585/848 X |
| 3,960,910 | 6/1976 | Sudduth et al. | 585/848 X |
| 4,014,950 | 3/1977 | Keyworth et al. | 585/848 X |
| 4,066,679 | 1/1978 | Long et al. | 585/848 X |
| 4,091,045 | 5/1978 | Walker | 585/848 X |

*Primary Examiner*—Paul F. Shaver
*Attorney, Agent, or Firm*—Evelyn Berlow

[57] ABSTRACT

In processes in which liquid sorbents that are solutions in an aromatic hydrocarbon or halogenated aromatic hydrocarbon of a bimetallic salt complex having the generic formula $M_I M_{II} X_n$.Aromatic, wherein $M_I$ is a Group I-B metal, $M_{II}$ is a Group III-A metal, X is halogen, n is the sum of the valences of $M_I$ and $M_{II}$, and Aromatic is an aromatic hydrocarbon or halogenated aromatic hydrocarbon are used to separate complexible ligand from a gas feedstream that comprises an olefin having 2 or 3 carbon atoms, alkylation of the aromatic hydrocarbon or halogenated aromatic hydrocarbon is inhibited by incorporating in the liquid sorbent a small amount of triphenylboron.

10 Claims, No Drawings

USE OF TRIPHENYLBORON AS ALKYLATION INHIBITOR IN A LIGAND-COMPLEXING PROCESS

This invention relates to an improved process for the separation of complexible ligands from gas feedstreams that utilizes complexing of the ligands with liquid sorbents that are solutions of bimetallic salt complexes having the generic formula $M_I M_{II} X_n$.Aromatic, wherein $M_I$ is a Group I-B metal, $M_{II}$ is a Group III-A metal, X is halogen, n is the sum of the valences of $M_I$ and $M_{II}$, and Aromatic is an aromatic hydrocarbon or halogenated aromatic hydrocarbon having 6 to 12 carbon atoms. The improvement comprises including in the liquid sorbent an amount of triphenylboron that will inhibit the alkylation of the aromatic component of the sorbent by lower olefins that are present in the gas feedstream.

Bimetallic salt complexes that have the generic formula $M_I M_{II} X_n$.Aromatic are known to be useful in the separation from gas mixtures of such complexible ligands as olefins, acetylenes, aromatics, and carbon monoxide. For example, in U.S. Pat. No. 3,651,159, Long et al. disclosed a process in which a sorbent solution of cuprous aluminum tetrahalide in toluene was used to separate ethylene, propylene, and other complexible ligands from a gas feedstream. The complexed ligands were recovered by ligand exchange with toluene. The resulting solution of cuprous aluminum tetrahalide.toluene in toluene was recycled and used to separate additional quantities of the complexible ligand from the gas feedstream. Walker et al. in U.S. Pat. No. 3,647,843 disclosed a process in which a hydrocarbon pyrolysis gas feedstream was contacted with a cuprous aluminum tetrachloride solution in toluene to separate acetylene from the gas feedstream as a solution of the complex HC≡CH.CuAlCl$_4$ in toluene. Acetylene was stripped from this complex, and the cuprous aluminum tetrachloride.toluene solution was recycled.

In processes such as those disclosed by Long et al. and by Walker et al. in which a liquid sorbent containing a bimetallic salt complex is recycled without purification and is used for long periods of time, there is a gradual increase in the amounts of reaction by-products and other impurities in it until sufficient impurities are present to interfere with the efficient operation of the process. For example, when the liquid sorbent is contacted with a gas stream that contains ethylene and/or propylene, some of the olefin reacts with the aromatic hydrocarbon or halogenated aromatic hydrocarbon in the sorbent to form alkylated aromatic compounds and some undergoes polymerization to form olefin oligomers. These reactions are catalyzed by hydrogen chloride or other acidic compounds that are in the gas feedstream or are formed as by-products of the reaction between the liquid sorbent and trace amounts of water or certain other impurities in the gas feedstream.

In ligand-separation processes that involve complexing of ligands with a liquid sorbent that is a solution of a bimetallic salt complex in an aromatic hydrocarbon, it is necessary to minimize the formation of alkylated aromatic compounds because the presence of these compounds not only adversely affects the complexing ability of the liquid sorbent, but also leads to corrosion of the processing equipment and copper metal deposition.

A number of procedures have been proposed in the prior art for inhibiting the reactions between the liquid sorbent and lower olefins to form alkylated aromatic compounds and olefin oligomers by removing or neutralizing the acidic materials that catalyze these reactions, but none has proven to be entirely satisfactory. Some of these procedures fail to reduce the amounts of reaction by-products to the desired very low levels, while others interfere with the efficient operation of the ligand-separation process. For example, Long et al. in U.S. Pat. Nos. 3,651,195; 3,887,600; 4,066,679; and 4,141,960 disclosed the use of a small amount of a neutralizing agent, such as ammonia or an organic nitrogen compound, to reduce the residual catalytic activity or acidity of the system. They taught that the amount of neutralizing agent should be merely enough to react with the free acidity of the system because larger amounts of the neutralizing agent will cause precipitation of copper salt from the solution and lead to the formation of different catalytic species. They preferred to use from 0.01 to 1 wt. percent, based on the liquid sorbent, of the neutralizing agent. Combinations of organic phosphines and organic nitrogen bases were used by Horowitz et al. in U.S. Pat. No. 3,758,609 to inhibit side reactions during olefin-complexing processes in which liquid sorbents containing cuprous aluminum tetrachloride were used as the complexing agent. The useful organic nitrogen bases included substituted pyridines, tertiary alkyl amines, and tertiary alkyl aryl amines. Pyridine was said to be ineffective as an inhibitor because it reacts with the liquid sorbent to form precipitates that contain sizeable amounts of the organic base. In U.S. Pat. Nos. 3,755,487 and 3,758,608, soluble compounds of antimony, arsenic, and bismuth, phosphines, amines, and other additives are added to liquid sorbents that comprise cuprous aluminum tetrachloride to minimize side reactions, to reduce the corrosion effect of the cuprous salt solution, and to prevent the deposition of copper from the solution. Tyler et al. in U.S. Pat. Nos. 3,776,972 and 3,933,878 disclosed that trialkyl phosphines and other complexible ligands can be used to inhibit alkylation and polymerization side reactions in olefin-complexing processes employing liquid sorbents that comprise cuprous aluminum tetrachloride and an aromatic hydrocarbon.

In accordance with this invention, it has been found that the alkylation and other side reactions that take place when a gas feedstream that comprises ethylene and/or propylene is contacted with a liquid sorbent that comprises a bimetallic salt complex of the formula $M_I M_{II} X_n$.Aromatic wherein $M_I$ is a Group I-B metal, $M_{II}$ is a Group III-A metal, X is halogen, n is the sum of the valences of $M_I$ and $M_{II}$, and Aromatic is an aromatic hydrocarbon or halogenated aromatic hydrogen having 6 to 12 carbon atoms can be substantially reduced by incorporating in the liquid sorbent an alkylation-inhibiting amount of triphenylboron. The presence of triphenylboron in the liquid sorbent makes it possible to reversibly absorb ethylene and/or propylene without encountering appreciable deterioration of the liquid sorbent resulting from reaction between the sorbent and the olefins, thereby lengthening the time that the sorbent can be used without purification in the ligand-separation process.

The liquid sorbents that are stabilized by the process of this invention are solutions of a bimetallic salt complex in an aromatic hydrocarbon or a halogenated aromatic hydrocarbon. The useful bimetallic salt complexes have the generic formula $M_I M_{II} X_n$.Aromatic. $M_I$ is a Group I-B metal; that is, copper, silver, or gold. Copper (I) is the preferred metal. $M_{II}$ is a Group III-A metal; that is, boron, aluminum, gallium, indium, or thallium. Boron and aluminum are the preferred metals, aluminum being particularly preferred. X is halogen, i.e., fluorine, chlorine, bromine, or iodine; it is preferably chlorine or bromine. The sum of the valences of $M_I$ and $M_{II}$ is represented by n. Aromatic is an aromatic hydrocarbon or halogenated aromatic hydrocarbon having 6 to 12 carbon atoms, and preferably 6 to 9 carbon atoms, such as benzene, toluene, ethylbenzene, xylene, mesitylene, chlorobenzene, bromobenzene, iodobenzene, dichlorobenzene, dibromobenzene, chlorotoluene, bromotoluene, iodotoluene, or chloroxylene. It is preferably benzene or toluene. Illustrative of these bimetallic salt complexes are the following: $CuBF_4$.benzene, $CuBCl_4$.benzene, $AgBF_4$.mesitylene, $AgBCl_4$.xylene, $AgAlCl_4$.xylene, $AgAlBr_4$.bromobenzene, $CuGaCl_4$.toluene, $CuInI_4$.1,2-dichlorobenzene, $Cu\,Tl\,I_4$.p-chlorotoluene, and the like. The preferred bimetallic salt complexes are $CuAlCl_4$.benzene, $CuAlCl_4$.toluene, and $CuAlBr_4$.benzene. The aromatic hydrocarbon or halogenated aromatic hydrocarbon in which the bimetallic salt complex is dissolved is usually and preferably the same as that used in the preparation of the bimetallic salt complex, but if desired it may be a different one. The total amount of aromatic hydrocarbon or halogenated aromatic hydrocarbon in the liquid sorbent, that is, the amount in the bimetallic salt complex plus the amount used as solvent, is at least 10 mole percent of the amount of the bimetallic salt $M_I M_{II} X_n$ that is present. It is preferred that the amount of aromatic hydrocarbon or halogenated aromatic hydrocarbon be 100 to 450 mole percent of the amount of the bimetallic salt. The particularly preferred liquid sorbents contain 25 to 75 percent by weight of $CuAlCl_4$.benzene in benzene or $CuAlCl_4$.toluene in toluene.

In the practice of this invention, a gas feedstream that contains ethylene, propylene, or a mixture thereof is contacted with a liquid sorbent that contains an alkylation-inhibiting amount of triphenylboron. When the gas feedstream is contacted with the inhibitor-containing sorbent, any water that is in the gas feedstream reacts with the cuprous aluminum tetrachloride in the liquid sorbent to form hydrogen chloride as a reaction by-product. The hydrogen chloride then reacts with the triphenylboron to form benzene and boron trichloride, which can readily be removed from the liquid sorbent. The reactions that take place when cuprous aluminum tetrachloride is contacted with water are shown in the following equations:

1. $2CuAlCl_4$.toluene$+H_2O \rightarrow HCl+CuCl+CuAlCl_4.Al(OH)Cl_2$.toluene

2. $CuAlCl_4.Al(OH)Cl_2$.toluene$\rightarrow HCl+CuAlCl_4.Al\,O\,Cl$.toluene

3. $2CuAlCl_4.Al\,O\,Cl$.toluene (solid)$+$toluene$\overset{\Delta}{\rightarrow} CuAlCl_4$.toluene$+Al\,O\,Cl+CuAlCl_4.Al\,O\,Cl$.toluene (liquid)

The reaction between triphenylboron and hydrogen chloride is shown in Equation 4:

4. $(C_6H_5)_3\,B+3HCl\rightarrow B\,Cl_3+3C_6H_6$

The amount of triphenylboron that is incorporated in the liquid sorbent is at least the amount that is required to react with the hydrogen chloride and other acidic compounds that are formed when the traces of water and certain other impurities in the gas feedstream react with the bimetallic salt complex in the liquid sorbent. In most cases, from about 0.1 mole percent to 20 mole percent, based on the copper or other Group I-B metal in the bimetallic salt complex, of triphenylboron is used. From 1 mole percent to 10 mole percent of triphenylboron is preferably used in the liquid sorbent to inhibit alkylation and other side reactions, with best results being obtained when from 2 mole percent to 5 mole percent of triphenylboron is used.

In the practice of this invention, all of the triphenylboron may be added to the liquid sorbent before the sorbent is contacted with the gas feedstream, or a minor portion (less than 50%) of the inhibitor may be present at the start of the ligand-separation process and the remainder added continuously or intermittently during the ligand-separation process at approximately the rate at which triphenylboron is being removed from the liquid sorbent by reaction with the hydrogen chloride resulting from the reaction between the liquid sorbent and water in the gas feedstream.

Either triphenylboron or a solution of triphenylboron in a liquid aromatic hydrocarbon or halogenated aromatic hydrocarbon may be added to the liquid sorbent. The triphenylboron is preferably added as a solution in benzene or toluene.

The triphenylboron that is used to stabilize the liquid sorbent by inhibiting alkylation of the aromatic compounds in it may be prepared by any suitable and convenient procedure. For example, it can be prepared by the Grignard reaction from phenyl magnesium bromide and boron trifluoride etherate. This procedure was described in detail by Krause and Nitsche in Ber. 55, 1261 (1922) and by Krause and Polack in Ber. 59, 777 (1926). Alternatively, it can be prepared by the procedure described by Wittig and Raff in Ann. 573, 195 (1951), which is shown in Equation 5:

5. $NaB\phi_4 \xrightarrow[H_2O]{(CH_3)_3N\,.\,HCl} [(CH_3)_3NH] + [B\phi_4] \xrightarrow[N_2]{200°\,C.} \phi H + (CH_3)_3N + \phi_3B$ Because triphenylboron reacts readily with oxygen, air must be excluded from the compound, from triphenylboron solutions, and from liquid sorbents that contain triphenylboron.

This procedure for the stabilization of liquid sorbents by inhibiting alkylation of the aromatic compounds in the sorbent is useful not only in processes in which ethylene and/or propylene is being separated from gas feedstreams but also in those in which carbon monoxide or another complexible ligand is being separated from a gas feedstream that contains trace amounts of the lower olefins as impurities.

The invention is further illustrated by the following examples.

EXAMPLE 1

A. A solution of cuprous aluminum tetrachloride in toluene was prepared by adding 1.1 moles of cuprous chloride to 1 mole of anhydrous aluminum chloride in toluene. The solution was filtered to remove unreacted cuprous chloride and insoluble impurities from it and then heated under vacuum to separate toluene and other volatile materials from the cuprous aluminum tetrachloride. The cuprous aluminum tetrachloride was dissolved in fresh toluene to form a liquid sorbent that had a density of 1.393 g./ml. and that contained 36.5 mmol of copper per 10 ml. of sorbent.

B. To a 10 ml. portion of the liquid sorbent was added a solution of 226 mg. of triphenylboron in 2 ml. of toluene to form a solution that contained 2.56 mole percent of triphenylboron, based on copper in the liquid sorbent.

C. The triphenylboron-containing liquid sorbent was contacted with propylene at 65° C. at an initial pressure of 720 torr for 3 hours. The final pressure was 370 torr, which was reached after about 15 minutes. The resulting liquid sorbent that contained the propylene-cuprous aluminum tetrachloride complex was stripped under vacuum to remove the propylene from it. The stripped liquid sorbent was then analyzed to determine the amount of alkylation that had taken place. The results obtained are summarized in Table I.

D. For comparative purposes, 10 ml. of the liquid sorbent that did not contain triphenylboron was contacted with propylene at 65° C. at an initial pressure of 720 torr for 0.5 hour. The resulting liquid sorbent that contained the propylene-cuprous aluminum tetrachloride complex was stripped under vacuum to remove the propylene from it, and the stripped liquid sorbent was analyzed to determine the amount of alkylation that had taken place. The results obtained are summarized in Table I.

TABLE I

Analysis of Inhibited and Uninhibited Liquid Sorbent After Contact With Propylene at 65° C.

| | Liquid Sorbent Containing 2.56 mole percent of Triphenylboron | Uninhibited Liquid Sorbent |
|---|---|---|
| Time of Contact with Propylene (Hours) | 3 | 0.5 |
| Analysis (mmol) | | |
| Monoisopropyltoluene | 0.00125 | 0.755 |
| Diisopropyltoluene | <0.00001 | 0.231 |
| Triisopropyltoluene | <0.00001 | 0.001 |
| Ratio — $\frac{\text{isopropyl}}{\text{copper}}$ | 0.00125 | 1.220 |

From the data in Table I, it will be seen that during the process in which propylene was contacted with a liquid sorbent that comprised cuprous aluminum tetrachloride and toluene, the alkylation of toluene was substantially inhibited by the addition of a small amount of triphenylboron to the liquid sorbent. The calculated inhibition factor is 5830.

EXAMPLE 2

A. A solution of cuprous aluminum tetrachloride in benzene was prepared by adding 1.1 moles of cuprous chloride to 1 mole of anhydrous aluminum chloride in benzene. The solution was filtered to remove unreacted cuprous chloride and insoluble impurities from it. The resulting liquid sorbent had a density of 1.204 g./ml., and it contained 20.0 mmol of copper per 10 ml. of sorbent.

B. To a 10 ml. portion of the liquid sorbent was added a solution of 143.5 mg. of triphenylboron in 1 ml. of benzene to form a solution that contained 2.96 mole percent of triphenylboron, based on copper in the liquid sorbent.

C. The triphenylboron-containing liquid sorbent was contacted with ethylene at 65° C. for 3 hours at an initial pressure of 720 torr. The resulting liquid sorbent that contained the ethylene-cuprous aluminum tetrachloride complex was stripped under vacuum to remove the ethylene from it. The stripped liquid sorbent was then analyzed to determine the amount of alkylation that had taken place. The results obtained are summarized in Table II.

D. For comparative purposes, 10 ml. of the liquid sorbent that did not contain triphenylboron was contacted with ethylene at 65° C. for 3 hours at an initial pressure of 720 torr. The resulting liquid sorbent was then stripped under vacuum to remove the ethylene from it and the stripped sorbent was analyzed to determine the amount of alkylation that had taken place. The results obtained are summarized in Table II.

The data in Table II demonstrate that during the process in which ethylene was contacted with a liquid sorbent that comprised cuprous aluminum tetrachloride and benzene, the alkylation of benzene was substantially inhibited by the presence of a small amount of triphenylboron to the liquid sorbent.

TABLE II

Analysis of Inhibited and Uninhibited Liquid Sorbent After Contact With Ethylene at 65° C.

| | Liquid Sorbent Containing 2.96 mole percent of Triphenylboron | Uninhibited Liquid Sorbent |
|---|---|---|
| Analysis (mmol) | | |
| Monoethylbenzene | 0.00796 | 0.0642 |
| Diethylbenzene | 0.00076 | 0.00191 |
| Triethylbenzene | 0.00067 | 0.00045 |
| Pentaethylbenzene | 0.00039 | 0.00097 |
| 1,1-Diphenylethane | 0.00131 | 0.00076 |
| Ratio — $\frac{\text{Ethyl}}{\text{Copper}}$ | 0.00129 | 0.06169 |

EXAMPLE 3

To 5 ml. of a liquid sorbent prepared by the procedure of Example 1A that had a density of 1.31 g./ml. and contained 14.3 mmol of cuprous aluminum tetrachloride was added 3 ml. of an 0.155 M triphenylboron solution in toluene. The resulting triphenylboron-containing sorbent was contacted with 3.6 mmol of ethylene at 80° C. for 3 hours. When the resulting reaction mixture was stripped twice under vacuum, 3.5 mmol of ethylene was recovered.

What is claimed is:

1. In the process for the separation of complexible ligands from a gas feedstream that comprises ethylene, propylene, or mixtures thereof wherein (a) said gas feedstream is contacted with a liquid sorbent that is a solution in an aromatic hydrocarbon or halogenated aromatic hydrocarbon of a bimetallic salt complex having the formula $M_I M_{II} X_n$.Aromatic, wherein $M_I$ is a Group I-B metal, $M_{II}$ is a Group III-A metal, X is halogen, n is the sum of the valences of $M_I$ and $M_{II}$, and Aromatic is an aromatic hydrocarbon or halogenated aromatic hydrocarbon having 6 to 12 carbon atoms, thereby forming a reaction mixture that comprises a solution of a complex of the complexible ligand and the bimetallic salt complex in the liquid sorbent, (b) the reaction mixture is separated from the gas feedstream, (c) the ligand is separated from the liquid sorbent in the reaction mixture, and (d) the liquid sorbent is recycled to Step (a), the improvements that comprise incorporating in said liquid sorbent from 0.1 mole percent to 20 mole percent, based on the Group I-B metal in the bimetallic salt complex component of the liquid sorbent, of triphenylboron and carrying out the ligand separation process in the substantial absence of oxygen, thereby substantially reducing alkylation and other side reactions and stabilizing said liquid sorbent.

2. The process of claim 1 wherein the liquid sorbent is a solution in an aromatic hydrocarbon or halogenated aromatic hydrocarbon of the bimetallic salt complex having the formula

CuAlCl$_4$.Aromatic

3. The process of claim 2 wherein the liquid sorbent is a solution of CuAlCl$_4$.toluene in toluene.

4. The process of claim 2 wherein the liquid sorbent is a solution of CuAlCl$_4$benzene in benzene.

5. The process of claim 2 wherein from 1 mole percent to 10 mole percent, based on the copper in the bimetallic salt complex component of the liquid sorbent, of triphenylboron is incorporated in the liquid sorbent.

6. The process of claim 2 wherein from 2 mole percent to 5 mole percent, based on the copper in the bimetallic salt complex component of the liquid sorbent, of triphenylboron is incorporated in the liquid sorbent.

7. The process of claim 1 wherein less than 50% of the triphenylboron is present at the start of the ligand-separation process, and the remainder is added continuously during the ligand-separation process.

8. The process of claim 1 wherein less than 50% of the triphenylboron is present at the start of the ligand-separation process, and the remainder is added intermittently during the ligand-separation process.

9. The process of claim 1 wherein a solution of triphenylboron in a liquid aromatic hydrocarbon or halogenated aromatic hydrocarbon is added to the liquid sorbent.

10. The process of claim 1 wherein a solution of triphenylboron in toluene is added to the liquid sorbent.

* * * * *